United States Patent [19]

Lerch et al.

[11] Patent Number: 5,015,642

[45] Date of Patent: May 14, 1991

[54] BENZOTHIAZINONE OXIDES, PROCESSES FOR THEIR PREPARATION, MEDICAMENTS CONTAINING THEM AND THE USE THEREOF, AND INTERMEDIATES FOR THEIR PREPARATION

[75] Inventors: Ulrich Lerch, Hofheim am Taunus; Rainer Henning, Hattersheim am Main; Hansjörg Urbach, Kronberg/Taunus; Joachim Kaiser, Frankfurt am Main, all of Fed. Rep. of Germany

[73] Assignee: Hoechst Aktiengesellschaft, Frankfurt am Main, Fed. Rep. of Germany

[21] Appl. No.: 230,407

[22] Filed: Aug. 10, 1988

[30] Foreign Application Priority Data

Aug. 12, 1987 [DE] Fed. Rep. of Germany ....... 3726759

[51] Int. Cl.$^5$ .................... A61K 31/38; C07D 279/16
[52] U.S. Cl. .................................. 514/224.2; 544/52
[58] Field of Search ...................... 544/52; 514/224.2

[56] References Cited

U.S. PATENT DOCUMENTS 4,584,300 4/1986 Iwo et al. ............................. 544/52
4,595,685 6/1986 Henning et al. ..................... 544/52

FOREIGN PATENT DOCUMENTS 0116368 8/1984 European Pat. Off. ............. 544/52
0243886 11/1987 European Pat. Off. ............. 544/52
0244723 11/1987 European Pat. Off. ............. 544/52
0146893 7/1988 European Pat. Off. ............. 544/52
1374283 11/1974 United Kingdom ................. 544/52

OTHER PUBLICATIONS

Chemical Abstracts, vol. 109, p. 32, Jul. 18, 1988.

*Primary Examiner*—Mary C. Lee
*Assistant Examiner*—J. Richter
*Attorney, Agent, or Firm*—Finnegan, Henderson, Farabow, Garrett, and Dunner

[57] ABSTRACT

Compounds I

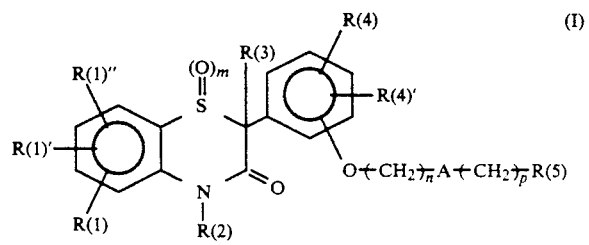

in which
R(1) and R(4) equal H, alkyl, alkoxy, Hal, $CF_3$, $NO_2$, · OH, acetamido or amino;
R(2) equals H, alk(en)yl or phenylalkyl (optionally substituted);
R(3) equals H, (cyclo)alk(en)yl-(alkyl), phenyl or phenylalkyl (optionally substituted);
A equal CHOH, CO, CH=CH, C≡C, $CH_2$, O or S;
m equals 1 or 2;
n equals 1 to 3;
p equals 0 to 4;
R(5) equals some amino groups, and their salts, exhibit excellent calcium-antagonistic activity.

Processes for their preparation are described.

5 Claims, No Drawings

BENZOTHIAZINONE OXIDES, PROCESSES FOR THEIR PREPARATION, MEDICAMENTS CONTAINING THEM AND THE USE THEREOF, AND INTERMEDIATES FOR THEIR PREPARATION

Benzothiazinone oxides, processes for their preparation, medicaments containing them and the use thereof, and intermediates for their preparation.

It is known that compounds which hinder the influx of calcium ions into cells can be used as therapeutics for the treatment of various diseases, in particular of the cardiovascular system in humans and other warm-blooded species.

Benzothiazinone derivatives having a calcium-antagonist action are described in U.S. Pat. No. 4 595 685 and have been proposed in German Patent Applications P 36 14 355.3, P 36 14 633.4 and P 37 24 366.7. It has now been found, surprisingly, that the 1-oxides and the 1,1-dioxides of the compounds described or proposed in the cited patent applications have a calciumantagonistic and/or cardiovascular action which is superior in some cases.

Hence have invention is directed at benzothiazinone oxides of the formula I

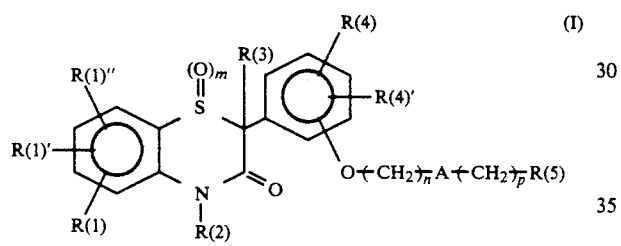

which have a calcium-antagonistic action, and their salts with pharmaceutically acceptable acids, in which formula I:

R(1), R(1)' and R(1)" are identical or different and denote, independently of one another, hydrogen, $(C_1-C_4)$-alkyl, $(C_1-C_3)$-alkoxy, F, Cl, Br, $CF_3$, nitro, hydroxyl, acetamido or amino, R(2) denotes hydrogen, $(C_1-C_{10})$-alkyl, straight-chain or branched, $(C_3-C_{10})$-alkenyl, straight-chain or branched, phenyl-$(C_1-C_4)$-alkyl, the phenyl ring being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy or nitro, R(3) denotes hydrogen, $(C_1-C_{15})$-alkyl, straight-chain or branched, $(C_3-C_{15})$-alkenyl, straight-chain or branched, $(C_4-C_8)$-cycloalkyl, $(C_4-C_8)$-cycloalkyl-$(C_1-C_4)$-alkyl, phenyl or phenyl-$(C_1-C_4)$-alkyl, the phenyl radical being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy or nitro, R(4) and R(4)' are identical or different and denote, independently of one another, hydrogen, $(C_1-C_4)$-alkyl, $(C_1-C_3)$-alkoxy, F, Cl, $CF_3$, nitro, hydroxyl, acetamido or amino, A denotes a CH(OH) group, a C=O group, a CH=CH group, a C≡C group, a $CH_2$ group, oxygen or sulfur, m denotes 1 or 2, n denotes 1, 2 or 3, p denotes zero, 1, 2, 3 or 4; but only 2, 3 or 4 where A is a heteroatom; and only 1, 2, 3 or 4 where A is a CH(OH), CH=CH or C≡C group, R(5) denotes one of the following groups

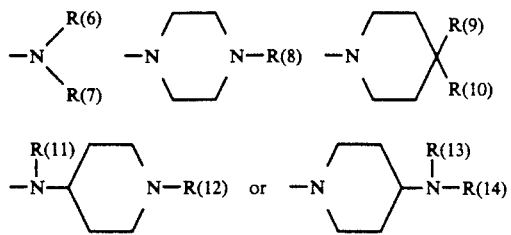

in which

R(6) and R(7) are identical or different and denote, independently of one another, hydrogen, $(C_1-C_{10})$-alkyl, $(C_4-C_8)$-cycloalkyl, $(C_4-C_8)$-cycloalkyl-$(C_1-C_4)$-alkyl, pyridyl-$(C_1-C_4)$-alkyl, phenyl-$(C_1-C_6)$-alkyl, benzhydryl or benzhydryl-$(C_1-C_4)$-alkyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(8) denotes hydrogen, $(C_1-C_{10})$-alkyl, straight-chain or branched, $(C_1-C_8-)$-alkanoyl, pyridyl, pyrimidinyl, phenyl, phenyl-$(C_1-C_4)$-alkyl, phenyl-$(C_3-C_{-5})$-alkenyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(9) denotes hydrogen, $(C_1-C_{10})$-alkyl, phenyl, phenyl-$(C_1-C_4)$-alkyl, each of the phenyl radicals being unsubstituted or substituted by one, two or three radicals from the group comprising $(C_1-C_4)$-alkyl, $(C_1-C_4)$-alkoxy, $(C_1-C_2-)$-alkylenedioxy, F, Cl, Br, $CF_3$ or hydroxyl, R(10) denotes hydrogen, hydroxyl or $(C_1-C_4)$-alkoxy, and R(11) and R(12) or R(13) and R(14) are identical or different and denote, independently of one another, hydrogen, $(C_1-C_{10})$-alkyl, straight-chain or branched, $(C_1-C_6)$-alkanoyl, phenyl-$(C_{1-4})$-alkyl, benzhydryl, or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, and the salts of the compounds of the formula I with pharmaceutically acceptable acids.

Preferred compounds of the formula I are those in which at least one of the substituents or indices has the following meaning:

R(1) and R(1)', identical or different and independently of one another, hydrogen, methyl, ethyl, methoxy, ethoxy, fluorine, chlorine, $CF_3$, nitro or acetamido, R(1)" hydrogen, R(2) hydrogen, $(C_1-C_6)$-alkyl, straight-chain or branched, allyl, methallyl, benzyl, phenethyl, 4-methoxybenzyl, 3,4-dimethoxybenzyl, 3,4,5-trimethoxybenzyl, 3,4-methylenedioxybenzyl, R(3) hydrogen, $(C_1-C_{12})$-alkyl, straight-chain or branched, allyl, methallyl, $(C_{5-7})$-cycloalkyl, $(C_{5-7})$-cycloalkyl-$(C_1-C_4)$-alkyl, benzyl, methylbenzyl, fluorobenzyl, methoxybenzyl, dimethoxybenzyl or phenylethyl, R(4) hydrogen, methyl, methoxy, ethoxy, fluorine, chlorine, nitro, hydroxyl, acetamido or amino, R(4)' hydrogen, A a CH(OH) group, a C=O group, a CH=CH group, a C≡C group, a $CH_2$ group, oxygen or sulfur, m 1 or 2, n 1 or 2, p zero, 1, 2 or 3; but only 2 or 3 when A is a heteroatom; and only 1, 2 or 3 where A is a CH(OH), CH=CH or C≡C group, R(5) one of the following groups

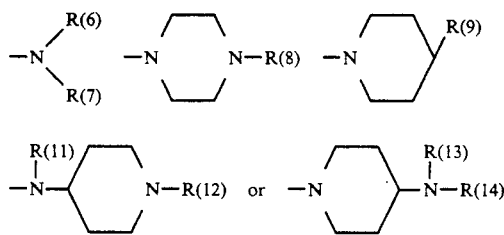

in which

R(6) denotes hydrogen, methyl, ethyl, propyl or isopropyl,

R(7) denotes hydrogen, methyl, ethyl, propyl, isopropyl, cyclopentylethyl, cyclohexylethyl, phenyl-$(C_1-C_4)$-alkyl, benzhydryl or benzhydryl-$(C_1-C_4)$-alkyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, $CF_3$ or hydroxyl, or denotes pyridyl-$(C_1-C_4)$-alkyl, R(8) denotes hydrogen, $(C_1-C_6)$-alkyl, straight-chain or branched, $(C_1-C_6)$-alkanoyl, phenyl, the phenyl radical being unsubstituted or substituted by one or two radicals from the group comprising $(C_1-C_4)$-alkyl, $(C_1-C_4)$-alkoxy, $(C_1-C_2)$-alkylenedioxy, F, Cl, $CF_3$ or hydroxyl, or denotes phenyl-$(C_1-C_4)$-alkyl, phenyl-$(C_{3-5})$-alkenyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising methyl, ethyl, methoxy, ethoxy, $(C_1-C_2)$-alkylenedioxy, F, Cl, $CF_3$ or hydroxyl, R(9) denotes phenyl, phenyl-$(C_1-C_4)$-alkyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, $CF_3$ or hydroxyl, R(10) denotes hydrogen, hydroxyl or methoxy, R(11), R(12), R(13) and R(14) are identical or different and denote hydrogen, $(C_1-C_8)$-alkyl, $(C_1-C_6)$-alkanyl, phenyl-$(C_1-C_4)$-alkyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising methyl, ethyl, methoxy, ethoxy, $(C_1-C_2)$-alkylenedioxy, F, Cl, $CF_3$ or hydroxyl, and the salts of these compounds of the formula I with pharmaceutically acceptable acids.

Particularly preferred compounds of the formula I are those in which at least one of the substituents or of the indices has the following meaning:

R(1) hydrogen, methyl, methoxy, fluorine or chlorine,

R(1)' hydrogen or methoxy,

R(1)'' hydrogen,

R(2) hydrogen, methyl, ethyl, propyl, isopropyl, butyl, sec.butyl, isobutyl, benzyl or phenethyl, R(3) hydrogen, $(C_1-C_{12})$-alkyl, straight-chain or branched, cyclopentyl, cyclohexyl, cyclopentylmethyl, cyclohexylmethyl, allyl, methallyl, benzyl, methylbenzyl, fluorobenzyl, methoxybenzyl, dimethoxybenzyl or phenylethyl, R(4) hydrogen, methoxy, methyl, fluorine, chlorine, nitro or hydroxyl, R(4)' hydrogen, A a CH(OH) group, a C=O group, a CH=CH group, a C≡C group, a $CH_2$ group or oxygen, m 1 or 2, n 1 or 2, p zero, 1 or 2; but only 2 when A is a heteroatom; and only 1 or 2 where A is a CH(OH), CH=CH or C≡C group, R(5) one of the following groups

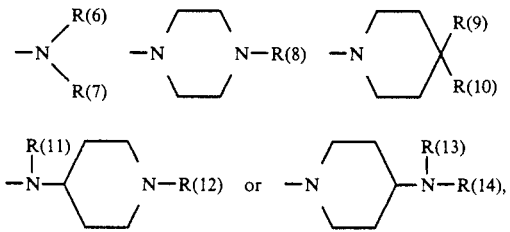

in which

R(6) denotes hydrogen or methyl,

R(7) denotes phenyl-$(C_1-C_4)$-alkyl, benzhydryl or benzhydryl-$(C_1-C_4)$-alkyl, each phenyl radical being unsubstituted or substituted by one, two or three radicals from the group comprising methyl, methoxy, fluorine, chlorine, methylenedioxy or hydroxyl, R(8) denotes $(C_1-C_6)$-alkyl, straight-chain or branched, $(C_1-C_6)$-alkanoyl, phenyl, phenyl-$(C_1-C_4)$-alkyl, benzhydryl or benzhydryl-$(C_1-C_4)$-alkyl, phenyl-$(C_{1-4})$-alkanoyl or benzoyl, each of the phenyl radicals being unsubstituted or substituted by one, two or three radicals from the group comprising methyl, methoxy, ethoxy, methylenedioxy, fluorine, chlorine or hydroxyl, R(9) denotes phenyl, the phenyl radical being unsubstituted or substituted by one, two or three radicals from the group comprising methyl, methoxy, fluorine, chlorine, methylenedioxy or hydroxyl, R(10) denotes hydrogen, hydroxyl or methoxy, R(11), R(12), R(13) and R(14) are identical or different and denote $(C_1-C_6)$-alkyl, $(C_1-C_6)$-alkanoyl, phenyl-$(C_1-C_4)$-alkyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising methyl, methoxy, methylenedioxy, fluorine, chlorine or hydroxyl, and the salts of these compounds of the formula I with pharmaceutically acceptable acids.

The pharmaceutically acceptable acids which are suitable are inorganic acids such as hydrochloric acid, hydrobromic acid, hydriodic acid, sulfuric acid, phosphoric acid or nitric acid, or organic acids such as tartaric acid, malic acid, lactic acid, maleic acid, fumaric acid, malonic acid, oxalic acid, gluconic acid, camphorsulfonic acid, benzenesulfonic acid, acetic acid, propionic acid or p-toluenesulfonic acid.

The compounds of the formula I have asymmetric carbon atoms and can thus occur as enantiomers or diastereomers. The invention embraces both the pure isomers and the mixtures thereof. These mixtures of diastereomers can be fractionated into the components by conventional methods, for example selective crystallization from suitable solvents or chromatography on silica gel or aluminum oxide. Customary methods can be used to fractionate the racemates into the individual enantiomers, for example by salt formation with optically active acids, such as camphorsulfonic acid or dibenzoyltartaric acid, and selective crystallization, or by derivatization with suitable optically active reagents, separation of the diasteromeric derivatives and cleavage again.

The invention also relates to processes for the preparation of compounds of the formula I, which comprise (a) reaction, under conditions of a nucleophilic substitution, of a compound of the formula II

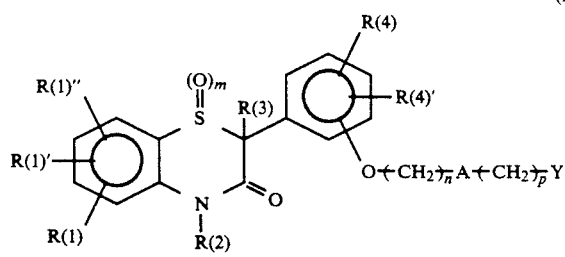

(II)

in which R(1), R(1)', R(1)'', R(2), R(3), R(4), R(4)', A, m, n and p have the same meaning as in formula I, and in which Y denotes a leaving group which can be displaced nucleophilically, in particular a chlorine, bromine or iodine atom, a radical of a sulfonic acid, preferably a methanesulfonyloxy radical, a benzenesulfonyloxy radical, a toluenesulfonyloxy radical or a trifluoromethanesulfonyloxy radical, with one of the compounds of the formulae IIIa, IIIb, IIIc, IIId or IIIe

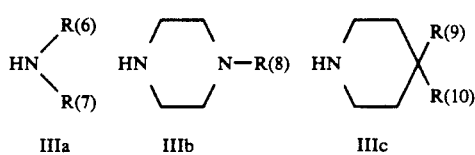

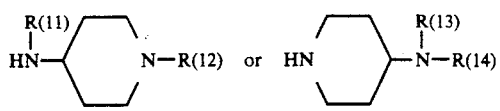

in which R(6), R(7), R(8), R(9), R(10), R(11), R(12), (13) and R(14) have the same meaning as in formula I, preferably in a polar organic solvent such as an alcohol, preferably methanol, ethanol, propanol or isopropanol, or a lower ketone, preferably acetone or methyl ethyl ketone, or dimethylformamide, dimethyl sulfoxide or sulfolane, or a hydrocarbon, preferably toluene, with or without the presence of an auxiliary base to trap the acid which is formed, preferably in the presence of potassium carbonate, sodium carbonate, triethylamine, N-ethylmorpholine or pyridine, at a temperature between 0 and 160° C., preferably between 20° and 120° C., or (b) reaction of a compound of the formula IV

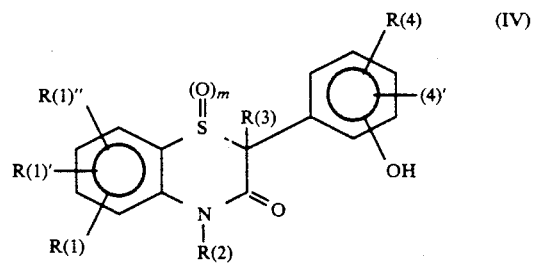

(IV)

in which R(1), R(1)', R(1)'', R(2), R(3), R(4), R(4)' and m have the same meaning as in formula I, with a compound of the formula V $$Z-(CH_2)_n-A-(CH_2)_p-R(5) \qquad (V)$$

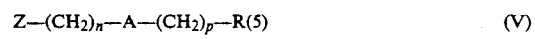

in which Z is defined in the same way as Y in formula II, and in which R(5) and A, n and p have the same meaning as in formula I, either in a polar aprotic solvent such as dimethylformamide, dimethyl sulfoxide, tetrahydroforan, sulfolane or N-methylpyrrolidone, in the presence of a strong base such as sodium hydride, potassium hydride, sodamide, lithium diisopropylamide, butyllithium or lithium hexamethyldisilazide, at a temperature between −40° and +60° C., preferably between −10° and −30° C., or in a protic or aprotic polar organic solvent such as a lower alcohol, for example methanol, ethanol or isopropanol, or a lower ketone, preferably acetone or methyl ethyl ketone, or in dimethylformamide, in the presence of a weak to moderately strong base, such as an alkali metal or alkaline earth metal hydroxide or carbonate, or an amine such as triethylamine, N-ethylmorpholine, N-methyldiisopropylamine or pyridine, at a temperature between 0° and 160° C., preferably between 20° and 120° C., or (c) reaction of a compound of the formula VI

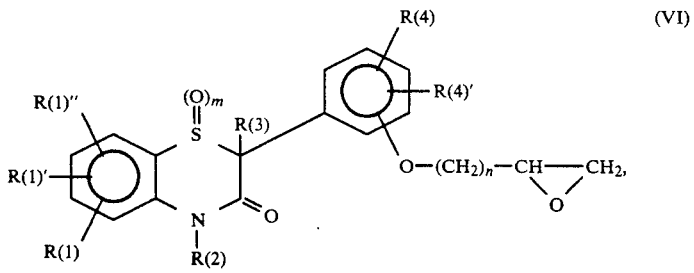
(VI)

in which R(1), R(1)', R(1)'', R(2), R(3), R(4), R(4)', m and n have the same meaning as in formula I, with amines of the formulae IIIa–IIIe without solvent or in the presence of a, preferably polar, solvent, such as methanol, isopropanol, acetone, THF or dimethylformamide, resulting in compounds of the formula I in which A denotes CH(OH) and p denotes 1, or (d) reaction, under amide-formation conditions known from the literature, of a compound of the formula VII

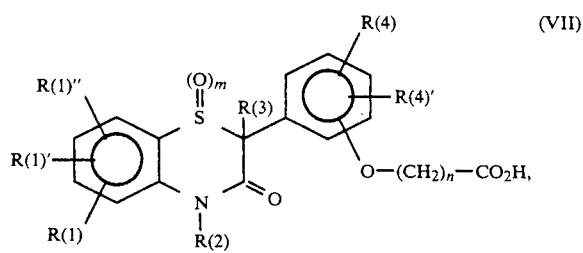
(VII)

in which R(1), R(1)', R(1)'', R(2), R(3), R(4), R(4)', m and n have the same meaning as in formula I, with one of the compounds of the formulae IIIa, IIIb, IIIc, IIId or IIIe, resulting in compounds of the formula I in which A denotes a C=O group and p denotes zero, or (e) oxidation of a compound of the formula VIII

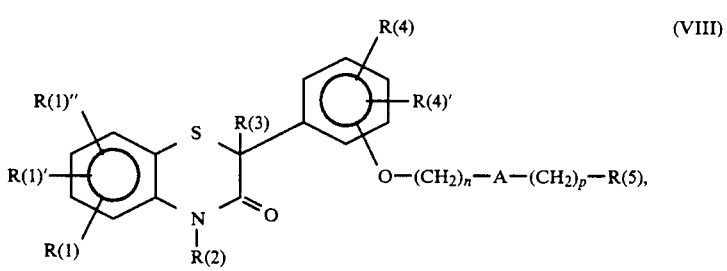
(VIII)

in which R(1), R(1)', R(1)'', R(2), R(3), R(4), R(4)', R(5), A, n and p have the same meaning as in formula I, with oxidizing agents which are known to convert thioethers into sulfoxides or sulfones, such as, for example, m-chloroperbenzoic acid, peracetic acid, hydrogen peroxide, potassium permanganate or chromic acid, to give compounds of the formula I.

Compounds of the formula VIII are described, for example, in German Offenlegungsschrift 3,347,173 and have been proposed in German Patent Applications P 36 14 355.3, P 35 14 363.4 and P 37 24 366.7.

Compounds of the formula II are obtained from compounds of the formula IX

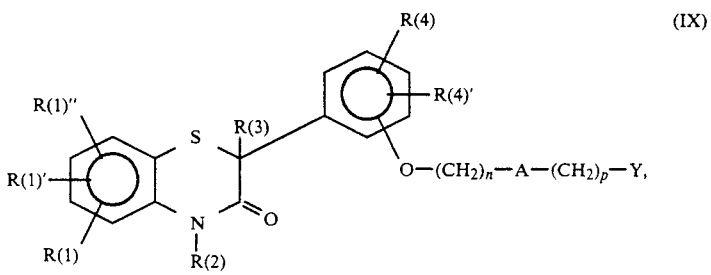
(IX)

in which R(1), R(1)', R(1)'', R(2), R(3), R(4), R(4)', A, m, n and p have the same meaning as in formula I, and in which Y has the same meaning as in formula II, with oxidizing agents under the conditions described in (e). Compounds of the formula IX have been described or proposed in the abovementioned German Offenlegungsschrift 3,347,173 or P 36 14 355.3, P 36 14 363.4 and P 37 24 366.7, respectively.

Compounds of the formula II can also be prepared from compounds of the formula IV and compounds of the formula X $$Z-(CH_2)_n-A-(CH_2)_p-Y \quad (X),$$

in which A, n and p have the same meaning as in formula I, Y has the same meaning as in formula II, and Z has the same meaning as in formula V.

Compounds of the formula IV are obtained from compounds of the formula XI

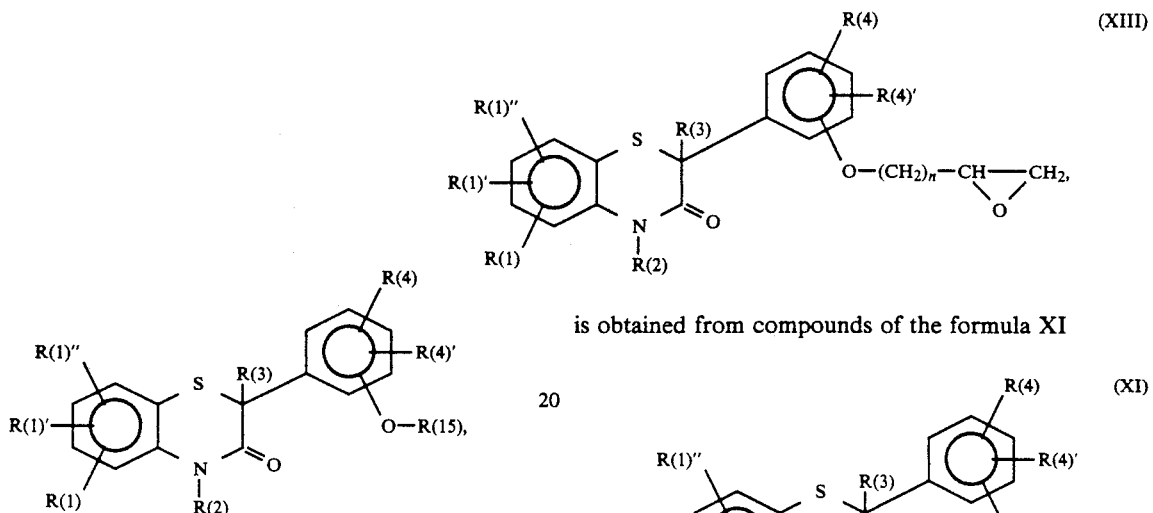

which R(1), R(1)', R(1)'', R(2), R(3), R(4) and R(4)' have the same meaning as in formula I, and R(15) represents hydrogen or a protective group which can be eliminated under mild conditions, for example a methyl, benzyl or acetyl group, with oxidizing agents under the conditions described in e) and, where appropriate, subsequent elimination of the protective group R(15) under suitable conditions, for example by catalytic hydrogenation for the benzyl group, reaction with boron tribromide, boron trichloride, trimethyliodosilane or pyridine hydrochloride for the methyl group, or potassium carbonate in alcoholic solution for the acetyl group. The preparation of the compounds of the formula XI is described, for example, in German Offenlegungsschrift 3,347,173. Compounds of the formula VI are obtained from compounds of the formula IV by alkylation using compounds of the formula XII

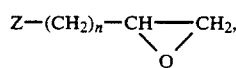  (XII)

in which Z has the same meaning as in formula V, under the conditions described for process (b).

Compounds of the formula VI can also be prepared from compounds of the formula XIII

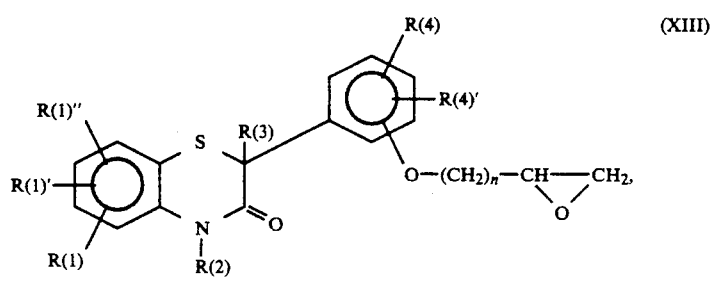

in which R(1), R(1)', R(1)'', R(2), R(3), R(4) and R(4)' have the same meaning as in formula I, by oxidation with oxidizing agents under the conditions described in (e). The preparation of compounds of the formula XIII is proposed, for example, in German Patent Application P 36 14 355.3:

A compound of the formula XIII

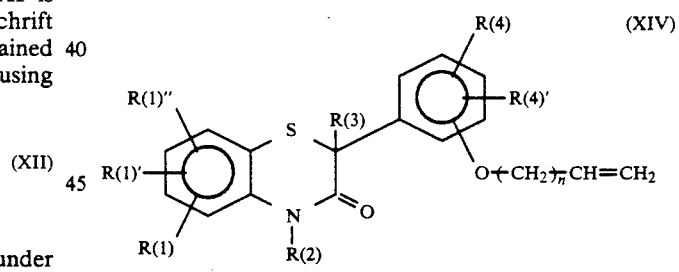

is obtained from compounds of the formula XI with R(15) equal to hydrogen, for example with epichlorohydrin and bases (for n=1) by known methods, or by alkylation of compounds of the formula XI with compounds of the formula X'

$$Z—(CH_2)—CH=CH_2 \qquad (X'),$$

in which n has the same meaning as in formula I, and in which Z has the same meaning as in formula X, there being formation of compounds of the formula XIV Subsequent epoxidation of the compounds by known processes, for example with m-chloroperbenzoic acid in methylene chloride yields compounds of the formula XIII.

Compounds of the formula VI can also be prepared from compounds of the formula XIV

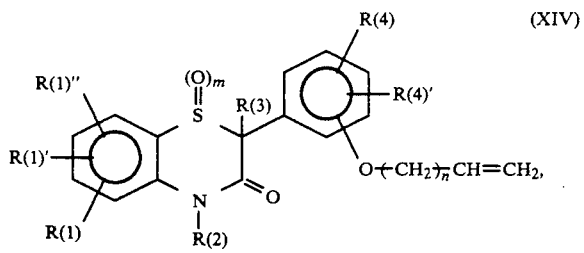

in which R(1), R(1)', R(1)'', R(2), R(3), R(4), R(4)', m and n have the same meaning as in formula I, by epoxidation by known processes, for example using m-chloroperbenzoic acid or peracetic acid in methylene chloride.

Compounds of the formula XIV are obtained from compounds of the formula IV by alkylation using compounds of the formula XV

in which n has the same meaning as in formula I, and Z has the same meaning as in formula V.

Compounds of the formula VII can be prepared from compounds of the formula IV by alkylation using compounds of the formula XVI

in which Z has the same meaning as in formula V, and R(16) denotes hydrogen or an alkyl radical, under the conditions described for process (b), or by oxidation of compounds of the formula XVII

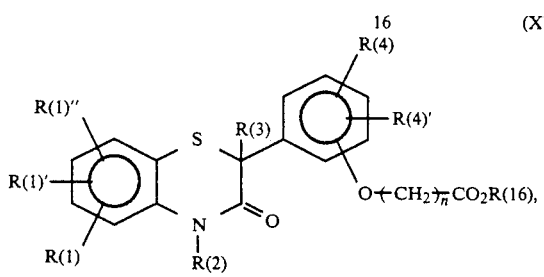

in which R(1), R(1)', R(1)'', R(2), R(3), R(4), R(4)' and n have the same meaning as in formula I, and R(16) has the same meaning as in formula XVI, with oxidizing agents as described under process (e).

Unless expressly mentioned otherwise, alkyl, alkylene, alkanoyl and alkoxy always mean straight or branched chains.

The compounds of the formula I, according to the invention, have pharmacological and biochemical actions, in particular calcium-antagonistic and blood-pressure lowering actions, and can thus be used for the treatment of all pathological states which derive from disturbance of the calcium balance in a warm-blooded animal.

Their calcium-antagonistic activity can be shown using the biochemical test model of the displacement of tritiumlabeled nitrendipine.

In this test, membrane preparations which contain isolated calcium channels are loaded with the labeled substance. After incubation with the test substance, the radioactivity which has been released into the supernatant solution is determined. The $IC_{50}$ values of the compounds of the formula I, according to the invention, in this model are from $10^{-6}$ molar to $10^{-10}$ molar Compounds of the formula I are also highly active in other test models with which it is possible to detect a calcium-antagonistic action, for example on the coronary perfusion in the isolated guinea pig heart, or on the action potential of the isolated guinea pig capillary muscle.

The compounds of the formula I, according to the invention, and their pharmacologically tolerated salts diminish the influx of calcium ions into cells and are thus suitable for the treatment of the cardiovascular system where there are appropriate symptoms, for example for various types of angina pectoris, tachycardia, cardiac dysrhythmias and high blood pressure. They are active in a wide dose range. The level of the dose administered depends on the nature of the desired treatment, on the mode of administration, on the condition, on the type and on the size of the treated mammal. On oral dosage, satisfactory results are obtained with doses of from 0.01, preferably from 0.1, in particular from 0.5, mg and up to 100 mg, preferably up to 20 mg, in particular up to 15 mg, of a compound of the formula I per kg of body weight. In humans, the daily dose varies from at least 10, in particular 20, mg to at most 800 mg, preferably 500 mg, it being possible to give single doses of 5 to 200 mg, in particular 5 to 100 mg, preferably once to three times a day. These data relate to an adult with a body weight of about 75 kg.

The dose for intravenous and intramuscular administration is at least 1 mg, prefararably at least 5 and at most 300 mg, preferably up to 150 mg a day.

The compounds of the present invention which can be used in pharmacology, and their salts, can be used for the preparation of pharmaceutical products which contain an effective amount of the active substance together with vehicles and which are suitable for enteral and parenteral administration. Use is preferably made of tablets or gelatin capsules which contain the active substance together with diluents, for example lactose, dextrose, sucrose, mannitol, sorbitol, cellulose and/or glycine, and lubricants such as diatomaceous earth, talc, stearic acid or its salts, such as magnesium or calcium stearate, and/or polyethylene glycol. Tablets additionally contain binders such as magnesium aluminum silicate, starch, gelatin, tragacanth, methylcellulose, sodium carboxymethylcellulose and/or polyvinylpyrrolidone and, if necessary, colorants, flavorings and sweeteners. Injectable products are preferably isotonic aqueous solutions or suspensions, which can be sterilized and contain auxiliaries such as preservatives, stabilizers, wetting agents and/or emulsifiers, solubilizers, salts to regulate the osmotic pressure, and/or buffer substances. The pharmaceutical products according to the invention, which, if desired, can contain. further pharmacologically valuable substances, are prepared, for example, by conventional mixing, granulating and coating processes, and contain 0.1% to about 75%, preferably about 1% to about 50%, of the active substance.

The examples which now follow are intended to illustrate the invention without confining it to these examples.

EXAMPLE 1

2-[2-[4-[4-[2-(3,4,5-Trimethoxyphenyl)ethyl]piperazin-1-yl]butoxy]phenyl]-2-isopropyl-4-methyl-2,3-dihydrobenzo-thiazin-3-one 1,1-dioxide (a) 7.2 g of 2-(2-[4-bromobutoxy]phenyl)-2-isopropyl-4-methyl-2,3-dihydrobenzothiazin-3-one 1,1-dioxide in 30 ml of DMF and 22.5 ml of 2N NaOH are heated at 80° to 90° C. with 7.82 g of 1-(2-[3,4,5-trimethoxyphenyl]-ethyl)piperazine dihydrochloride for 4 hours. The reaction mixture is poured onto 300 ml of ice-water and extracted several times with ethyl acetate. The combined organic phases are washed with water, dried and concentrated in vacuo. The residue is chromatographed on 200 g of silica gel (eluent dichloromethane/methanol 9:1). After evaporation of the product fractions, the dihydrochloride is precipitated from ethanol using ethanolic HCl, and is recrystallized from ethanol. Melting point 223°–224° C.

$^1$H NMR (base): δ=6.45–8.0 (m, 8H), 6.40 (s, 2H), 3.80 (s, 6H), 3.77 (s, 3H), 3.45 (s, 3H), 1.40–2.0 (m, 4H), 1.25 (d, 3H), 1.07 (d, 3H).

(b) The 2-(2-[4-bromobutoxy]phenyl)-2-isopropyl-4-methyl-2,3-dihydrobenzothiazin-3-one 1,1-dioxide used as starting material can be prepared as follows:

8.9 g of 2-(2-[4-bromobutoxy]phenyl)-2-isopropyl-4-methyl-2,3-dihydrobenzothiazin-3-one are dissolved in 400 ml of dichloromethane, and 17.2 g of 3-chloroperbenzoic acid are added in portions at room temperature. The reaction mixture is then stirred for 4 hours and subsequently washed 5 times with saturated NaHCO$_3$ solution. The organic phase is dried with sodium sulfate and concentrated in vacuo. The product crystallizes on standing overnight.

Melting point 118° to 120° C.

$^1$H NMR: δ=6.5–8.0 (m, 8H), 3.83 (m, 2H), 3.45 (s, 3H), 2.8–3.6 (m, 3H), 1.6–2.2 (m, 4H), 1.08 (dd, 6H).

EXAMPLE 2

(+)-Enantiomer of 2-[2-[4-[4-[2-(3,4,5-trimethoxyphenyl)ethyl]piperazin-1-yl]butoxy]phenyl]-2-isopropyl-4-methyl-2,3-dihydrobenzothiazin-3-one 1,1-dioxide The preparation is carried out in analogy to Example 1, using the (+)-enantiomer of 2-(2-[4-bromobutoxy]phenyl)-2-isopropyl-4-methyl-2,3-dihydrobenzothiazin-3-one 1,1-dioxide as reactant.

The dihydrochloride melts at 243°–4° C. (decomposition).

$^1$H NMR (base): =6.5–7.9 (m, 8H), 6.35 (s, 2H), 3.84 (s, 6H), 3.80 (s, 3H), 3.43 (s, 3H), 1.5–1.9 (m, 4H), 1.27 (d, 3H), 1.15 (dd, 6H).

EXAMPLE 3

(−)-Enantiomer of 2-[2-[4-[4-[2-(3,4,5-trimethoxyphenyl)ethyl]piperazin-1-yl]butoxy]phenyl]-2-isopropyl-4-methyl2,3-dihydrobenzothiazin-3-one 1,1-dioxide The preparation is carried out in analogy to that of the racemic compound (Example 1a) using the (−)-enantiomer of 2-(2-[4-bromobutoxy]phenyl)-2-isopropyl-4-methyl-2,3-dihydrobenzothiazin-3-one 1,1-dioxide. The dihydrochloride melts at 241°–3° C. (decomposition).

The $^1$H NMR spectrum is identical to that of the (+)-enantiomer (Example 2).

EXAMPLE 4

2-[2-[4-[4-(3,4,5-Trimethoxyphenylacetyl)piperazin-1-yl]butoxy]phenyl]-2-isopropyl-4-methyl-2,3-dihydrobenzothia-zin-3-one 1,1-dioxide Preparation in analogy to Example 1 a from 2-(2-[4-bromobutoxy]-phenyl)-2-isoprDpyl-4-methyl-2,3-dihydrobenzothiazi-3-one 1,1-dioxide and 1-(2-[3,4,5-trimethoxyphenyl]acetyl)piperazine. Hydrochloride melting point 145° C.

$^1$H NMR (base): δ=6.53–8.05 (m, 8H), 6.43 (s, 2H), 3.83 (s, 6H), 3.80 (s, 3H), 3.65 (s, 2H), 3.43 (m, 3H), 1.70 (m, 4H), 1.16 (dd, 6H).

EXAMPLE 5

(+)-Enantiomer of 2-[2-[4-[4-[N-methyl-2-(3,4,5-trimethoxyphenyl)ethylamino]piperidin-1-yl]butoxy]phenyl]-2-isopropyl-4-methyl-2,3-dihydrobenzothiazin-3-one 1,1-dioxide.

The synthesis is carried out in analogy to Example 1a from (+)-2-(2-[4-bromobutoxy]phenyl)-2-isopropyl-4-methyl-2,3-dihydrobenzothiazin-3-one 1,1-dioxide and 4-(N-methyl-2-[3,4,5-trimethoxyphenyl]ethylamino)-piperazine.

$^1$H NMR: δ=6.5–8.0 (m, 8H), 6.40 (s, 2H), 3.80 (s, 6H), 3.76 (s, 3H), 3.43 (s, 3H), 1.4–2.2 (m, 8H), 0,9–1.4 (dd, 6H).

EXAMPLE 6

2-[2-[4-[4-[2-(3,4,5-Trimethoxyphenyl)ethyl]piperazin-1yl]butoxy]phenyl]-2-benzyl-4-methyl-2,3-dihydrobenzothiazin-3-one 1,1-dioxide The synthesis is carried out in analogy to Example 1a from 2-(2-[4-bromobutoxy]phenyl)-2-benzyl-4-methyl-2,3-dihydrobenzothiazin-3-one 1,1-dioxide and 1-(2-[3,4,5trimethoxyphenyl]ethyl)piperazine. Dihydrochloride melting point 201°–3° C. (decomposition)

$^1$H NMR (base) δ=6.45–7.8 (m, 8H), 6.9 (s, 5H), 6.38 (s, 2H), 3.80 (s, 6H), 3.77 (s, 3H), 3.37 (s, 3H), 3.2–4.2 (m, 4H), 2.0–2.8 (m, 14H), 1.2–1.8 (m, 4H).

The 2-(2-[4-bromobutoxy]phenyl)-2-benzyl-4-methyl-2,3-dihydrobenzothiazin-3-one 1,1-dioxide required as starting material is prepared by oxidation of 2-(2-[4-bromobutoxy]phenyl)-2-benzyl-4-methyl-2,3-dihydrobenzothiazin-3-one in analogy to Example 1b.

EXAMPLE 7

2-[2-[4-[N-Methyl-2-(3,4-dimethoxyphenyl)ethylamino]butoxy]phenyl]-2-benzyl-4-methyl-2,3-dihydrobenzothiazin-3-one 1,1-dioxide The preparation is carried out in analogy to Example 1a using N-methylhomoveratrylamine as base.

Oxalate: melting point 161°–163° C.

$^1$H NMR: δ=6.5–7.8 (m, 11H), 6.86 (s, 5H), 3.8 (s, 6H), 3.33 (s, 3H), 3.3–4.2 (s, 4H), 2.2–3.0 (m, 6H), 2.30 (s, 3H), 1.2–2.0 (m, 4H).

EXAMPLE 8

2-[2-[4-[4-[2-(3,4,5-Trimethoxyphenyl)ethyl]piperazin-1yl]butoxy]-5-fluorophenyl]-2-isopropyl-4-methyl-2,3-dihydrobenzothiazin-3-one 1,1-dioxide The preparation is carried out in analogy to Example 1a from 2-(2-[4-bromobutoxy]-5-fluorophenyl)-2-isopropyl-4-methyl-2,3-dihydrobenzothiazin -3-one 1,1-dioxide. Dihydrochloride: melting point 224°–226° C.

¹H NMR: δ=6.6-8.2 (m, 7H), 6.45 (s, 2H), 3.85 (s, 6H), 3.80 (s, 3H), 3.50 (s, 3H), 1.80 (s, 4H), 1.20 (dd, 6H).

EXAMPLE 9

2-[2-[4-[4-[2-(3,4,5-Trimethoxyphenyl)ethyl]piperazin-1-yl]but-2-ynoxy]-5-fluorophenyl]-2-isopropyl-4-methyl-2,3-dihydrobenzothiazin-3-one 1,1-dioxide (a) The preparation is carried out in analogy to Example 1a from 2-2-[4-chlorobut-2-ynoxy]-5-fluorophenyl)-2-isopropyl -4-methyl-2,3-dihydrobenzothiazin-3-one 1,1-dioxide and 1-(2-[3,4,5-trimethoxyphenyl]ethyl)piperazine.

Dihydrochloride: melting point 160°-162° C. ¹H NMR: δ=7.63-7.7 (m, 2H), 7.3-7.4 (m, 1H), 6.95 7.03 (m, 2H), 6.68-6.80 (m, 2H), 6.37 (s, 2H), 4.51 (m, 2H), 3.79 (s, 6H), 3.75 (s, 3H), 3.45 (s, 3H), 3.23 (m, 2H), 3.12 (m, 1H), 2.4-2.8 (m, 12H), 1.15 (dd, 6H).

The 2-(2-[4-chlorobut-2-ynoxy]-5-fluorophenyl)-2-isopropyl -4-methyl-2,3-dihydrobenzothiazin-3-one 1,1dioxide used as starting material is prepared as follows:

(b) 13.4 g of 3-chloroperbenzoic acid are added in portions to 8.28 g of 2-(2-hydroxy-5-fluorophenyl)-2-isopropyl-4-methyl-2,3-dihydrobenzothiazin-3-one in 400 ml of dichloromethane at room temperature. The mixture is then stirred for 2 hours, and is washed with 3×100 ml of saturated sodium bicarbonate solution. The organic phase is dried and concentrated in vacuo. The oily dioxide is obtained.

¹H NMR: δ=6.4-8.0 (m, 8H), 3.48 (s, 3H), 1.2 (dd, 6H).

(c) 9.08 of the crude phenol derivative obtained in Example 9b are stirred under reflux in 150 ml of 2-butanone and 10.35 g of ground potassium carbonate with 7.3 ml of 1,4-dichloro-2-butyne for 5 hours. After cooling, the precipitate is filtered off with suction, and the filtrate is concentrated in vacuo. The remaining oil is purified by chromatography on SiO₂.

(Eluent cyclohexane/ethyl acetate 3:1).

¹H NMR: δ=6.6-7.85 (m, 7H), 4.62 (m, 2H), 4.16 (m, 2H), 3.55 (s, 3H), 3.2 (m, 1H), 1.23 (dd, 6H).

EXAMPLE 10

2-[2-[4-[4-[2-(3,4,5-Trimethoxyphenyl)ethyl]piperazin-1-yl]but-2-enoxy]-5-fluorophenyl]-2-isopropyl-4-methyl-2,3-dihydrobenzothiazin-3-one 1,1-dioxide 2.0 g of the acetylene derivative described in Example 9a are dissolved in 10 ml of pyridine, and 0.2 g of Pd/BaSO4 is added. The mixture is shaken in a hydrogenation apparatus until the calculated amount of hydrogen has been taken up. After the catalyst has been removed, and the solvent has been evaporated off, there is obtained a crude product which is purified on 80 g of SiO₂ using dichloromethane/methanol 98:2 as eluent.

Dihydrochloride: melting point 183°-185° C.

¹H NMR (base): δ=7.65-7.8 (m, 2H), 7.44 (m, 1H), 6.97-7.13 (m, 2H), 6.78-6.9 (m, 1H), 6.64-6.73 (m, 1H), 6.45 (s, 2H), 5.75 (m, 2H), 4.5 (m, 2H), 3.87 (s, 6H), 3.83 (m, 3H), 3.2 (m, 1H), 3.05 (m, 2H), 20 2.4-2.8 (m), 1.1-1.4 (m, 6H).

EXAMPLE 11

2-[2-[4-[4-[2-(3,4,5-Trimethoxyphenyl)ethyl]piperazin-1-yl]but-2-ynoxy]-5-fluorophenyl]-7-fluoro-2-isopropyl-4-methyl-2,3-dihydrobenzothiazin-3-one 1,1-dioxide The preparation is carried out in analogy to Example 9.

Dihydrochloride: melting point 206°-208° C.

¹H NMR (base): δ=7.7 (m, 1H), 7.45 (dd, 1H), 7.1 (m, 2H), 6.84 (m, 2H), 6.43 (s, 2H), 4.58 (m, 2H), 3.85 (s, 6H), 3.82 (s, 3H), 3.50 (s, 3H), 3.30 (m, 2H), 3.17 (m, 1H), 2.75 (m, 2H), 2.60 (m, 10H), 1.26 (d, 3H), 1.16 (d, 3H).

EXAMPLE 12

2-[2-[4-[4-[2-(3,4,5-Trimethoxyphenyl)ethyl]piperazin-1-yl]but-2-enoxy]-5-fluorophenyl]-7-fluoro-2-isopropyl-4-methyl-2,3-dihydrobenzothiazin-3-one 1,1-dioxide The preparation from the compound from Example 11 is carried out in analogy to Example 10.

Dihydrochloride: melting point 230°-232° C.

¹H NMR (base): δ=7.68 (dd, 1H), 7.47 (dd, 1H), 7.13 (m, 1H), 6.98 (dd, 1H), 6.86 (m, 1H), 6.19 (dd, 1H), 6.43 (s, 2H), 5.74 (m, 2H), 4.48 (m, 2H), 3.85 (s, 6H), 3.8 (s, 3H), 3.43 (s, 3H), 3.17 (m, 1H), 1.25 (d, 3H), 1.13 (d, 3H).

EXAMPLE 13

2-[2-[3-[4-[2-(3,4,5-Trimethoxyphenyl)ethyl]piperazin-1-yl]-2-hydroxypropoxy]phenyl]-2-ethyl-4,7-dimethyl-2,3-dihydrobenzothiazin-3-one 1,1-dioxide The preparation is carried out from 2-(2-[2,3-epoxypropoxy]phenyl)-2-ethyl-4,7-dimethyl-2,3-dihydrobenzothiazinone 1,1-dioxide and 1-(2-[3,4,5-trimethoxyphenyl]ethyl)piperazine.

¹H NMR (base): δ=6.45-7.95 (m, 7H), 6.40 (s, 2H), 3.80 (s, 6H), 3.76 (s, 3H), 3.45 (s, 3H), 2.4 (s, 3H).

EXAMPLE 14

2-[2-[4-[4-[2-(3,4,5-Trimethoxyphenyl)ethyl]piperazin-1-yl]-4-oxobutoxy]phenyl]-2-cyclohexyl-4-methyl-2,3-dihydrobenzothiazin-3-one 1,1-dioxide 3.2 g of 2-(2-[3-carboxypropoxy]phenyl)-2-cyclohexyl-4-methyl-2,3-dihydrobenzothiazin-3-one 1,1-dioxide in 15 ml of DMF are stirred at room temperature with 1.05 g of hydroxybenzotriazole, 2.1 g of 1-(2-[3,4,5-trimethoxy-phenyl]ethyl)piperazine and 1.85 g of dicyclohexylcarbodiimide for 2 hours. The mixture is left to stand overnight, the crystals are filtered off with suction, the filtrate is poured onto 100 ml of ice-water, and the mixture is extracted 3 x with ethyl acetate. The combined organic phases are washed with bicarbonate solution and water, dried and evaporated. The residue is purified on silica gel (120 g) using methylene chloride/methanol 9:1.

¹H NMR δ=6.45-8.0 (m, 8H), 6.43 (s, 2H), 3.81 (s, 6H), 3.78 (s, 3H), 3.43 (s, 3H), 0.9-2.0 (s, 13H).

EXAMPLE 15

(+)-Enantiomer of 2-[2-[5-(4-[2-(3,4,5-trimethoxyphenyl)ethyl]piperazin-1-yl]-3-oxapentyloxy]phenyl]-2-isopropyl-4-methyl -2,3-dihydrobenzothiazin-3-one 1,1-dioxide (a) Preparation is carried out in analogy to Example 1a from (+)-2-(2-[5-bromo-3-oxapentyloxy]phenyl)-2-isopropyl -4-methyl-2,3-dihydrobenzothiazin-3-one 1,1dioxide and 1-(2-[3,4,5-trimethoxyphenyl]ethyl)piperazine $^1$H NMR: δ=6.45–7.9 (m, 8H), 6.35 (s, 2H), 3.80 (s, 6H), 3.77 (s, 3H), 3.40 (s, 3H), 2.9–4.1 (m, 7H), 2.3–2.8 (m, 14H), 1.17 (dd, 6H).

Oxalate: melting point 209°–211° C. (decomposition)

(b) The (+)-2-(2-[5-bromo-3-oxapentyloxy]phenyl)-2-isopropyl -4-methyl-2,3-dihydrobenzothiazin-3-one 1,1dioxide which is required as starting material is prepared in analogy to Example 1b from (+)-2-(2-[5-bromo -3-oxapentyloxy]phenyl)-2-isopropyl-4-methyl-2,3-dihydrobenzothiazin-3-one by oxidation with 3chloroperbenzoic acid.

EXAMPLE 16

2-[3-[3-(4-[2-(3,4,5-Trimethoxybenzoyl)ethyl]piperazin-1-yl)
-propoxy]phenyl]-2-isopropyl-4-methyl-2,3-dihydrobenzothiazin-3-one 1,1-dioxide The preparation is carried out in analogy to Example 1a from 2-(3-[3-bromopropoxy]phenyl)-2-isopropyl-4-methyl-2,3-dihydrobenzothiazin-3-one 1,1-dioxide.

$^1$H NMR: =6.5–8.0 (m, 8H), 6.65 (s, 2H), 3.78 (s, 6H), 3.67 (S, 3H), 3.40 (s, 3H) 1.1 (dd, 6H).

EXAMPLE 17

2-[2-[4-(1-[3,4-Dimethoxyphenyl)-2-methyl-2-propylamino]butoxy]phenyl]-2,4-dimethyl-2,3-dihydrobenzothiazin-3-one 1-oxide (a) The preparation is carried out as described in Example 1a from 2-(2-[4-bromobutoxy]phenyl)-2,4-dimethyl-2,3-dihydrobenzothiazin-3-one 1-oxide.and 1-(3,4-dimethoxy-phenyl)-2-methyl-2-propylamine $^1$H NMR: δ=6.5–7.7 (m, 11H), 3.75 (s, 6H), 3.45 (s, 3H), 1.0 (s, 6H).

Hydrochloride: melting point 215° C.

(b) The sulfoxide required as starting material is prepared as follows: 8.08 g of 2-(2-[bromobutoxy]phenyl)-2,4-dimethyl-2,3-dihydrobenzothiazin-3-one are dissolved in 200 ml of dichloromethane and, at room temperature, 3-chloroperbenzoic acid is added in portions until the starting material has reacted completely (TLC check with chloroform/methanol 95:5 as mobile phase). About 5.3 g of 80 to 90% pure 3-chloroperbenzoic acid are required. After subsequent stirring for 1 hour, the organic phase is washed 3 x with saturated bicarbonate solution, dried and concentrated in vacuo.

EXAMPLE 18

2-[2-[4-[4-[2-(3,4,5-Trimethoxyphenyl)ethyl]piperazin-1yl]butoxy]phenyl]-2-isopropyl-4-methyl-2,3-dihydrobenzothiazin-3-one 1-oxide The preparation is carried out in analogy to Example 1a from 2-(2-[4-bromobutoxy]phenyl)-2-isopropyl-4-methyl-2,3-dihydrobenzothiazin-3-one 1-oxide (prepared in analogy to Example 17b) and 1-(2-[3,4,5-trimethoxyphenyl]ethyl)piperazine $^1$H NMR: δ=6.4–7.6 (m, 8H), 6.35 (s, 2H), 3.81 (s, 6H), 3.77 (s, 3H), 3.44 (s, 3H), 2.3–2.8 (s, 14H), 1.5–2.1 (m, 4H), 1.0–1.4 (m, 6H).

Dihydrochloride: melting point 248°–250° C.

EXAMPLE 19

(+)-Enantiomer of
2-[2-[4-[4-(2-(3,4,5-trimethoxyphenyl)ethyl]piperazin-1-yl)butoxy]phenyl]-2-isopropyl-4-methyl-2,3-dihydrobenzothiazin-3-one 1-oxide The preparation is carried as for the racemic compound (Example 18) but from the (+)-enantiomer of 2-(2-[4-bromobutoxy]phenyl-2-isopropyl-4-methyl-2,3-dihydrobenzothiazin-3-one 1-oxide.

$^1$H NMR: δ=6.5–7.6 (m, 8H), 6.40 (s, 2H), 3.83 (s, 6H), 3.80 (s, 3H), 3.45 (s, 3H), 1.80 (m, 4H), 1.12 (dd, 6H).

Dihydrochloride: melting point 198°–200° C. (from isopropanol). cl EXAMPLE 20

(−)-Enantiomer of
2-[2-[4-14-[2-(3,4,5-trimethoxyphenyl)ethyl]piperazin-1-yl]butoxy]phenyl]-2-isopropyl-4-methyl-2,3-dihydrobenzothiazin-3-one 1-oxide The preparation is carried out as for the racemic compound (Example 18), from the (−)-enantiomer of 2-(2-[4-bromobutoxy] phenyl)-2-isopropyl-4-methyl-2,3-dihydrobenzothiazin-3-one 1-oxide.

$^1$H NMR: δ=6.5–7.6 (m, 8H), 6.40 (s, 2H), 3.8 (s, 6H), 3.75 (s, 3H), 3.45 (s, 3H), 1.75 (m, 4H), 1.1 (dd, 6H).

Dihydrochloride: melting point 215°–217° C.

EXAMPLE 21

(+)-Enantiomer of
2-[2-[4-[4-[N-methyl-2-(3,4,5-trimethoxyphenyl)ethylamino]piperidin-1-yl]butoxy]phenyl]-2-isopropyl -4-methyl-2,3-dihydrobenzothiazin-3-one 1-oxide The preparation is carried out in analogy to Example 1a from (+)-2-(2-[4-bromobutoxy]phenyl)-2-isopropyl-4-methyl-2,3-dihydrobenzothiazin-3-one 1-oxide and 4-(N-methyl-2[3,4,5-trimethoxyphenyl]ethylamino)-piperidine $^1$H NMR: δ=6.4–7.5 (m, 8H), 6.35 (s, 2H), 3.80 (s, 6H), 3.75 (s, 3H), 3.43 (s, 3H), 1.4–2.2 (m, 8H), 0.97–1.4 (dd, 6H).

Melting point (dihydrochloride): 93°–95° C.

EXAMPLE 22

2-[2-[4-[4-[2-(3,4,5-Trimethoxyphenyl)ethyl]piperazin-1yl]butoxy]phenyl]-2-benzyl-4-methyl-2,3-dihydrobenzothiazin-3-one 1-oxide The preparation is carried out in analogy to Example 1a from 2-(2-[4-bromobutoxy]phenyl)-2-benzyl-4-methyl-2,3- dihydrobenzothiazin-3-one 1-oxide $^1$H NMR: δ=6.5–7.6 (m, 13H), 6.40 (s, 2H), 3.82 (s, 6H), b 3.77 (s, 3H), 3.47 (s, 3H), 1.4–1.9 (m, 4H).

Oxalate: melting point 195°–7° C. (decomposition).

EXAMPLE 23 b
2-[2-[4-(N-Methyl-2-[3,4-dimethoxyphenyl)ethylamino]butoxy]phenyl]-2-benzyl-4-methyl-2,3-dihydrobenzothiazin-3-one 1-oxide The preparation is carried out in analogy to Example 1a from 2-(2-[4-bromobutoxy]phenyl)-2-benzyl-4-methyl-2,3- dihydrobenzothiazin-3-one 1-oxide and N-methylhomoveratrylamine $^1$H NMR δ6.3–7.6 (m, 11H), 6.75 (s, 5H), 8.3 (s, 3H), 8.0 (s, 3H), 3.47 (s, 3H), 1.3–1.8 (m, 4H).

EXAMPLE 24

(+)-Enantiomer of 2-(2-[5-(4-[2-(3,4,5-Trimethoxyphenyl)ethyl]piperazin-1-yl]-3-oxapentyloxy]phenyl)-2-isopropyl-4-methyl-2,3-dihydrobenzothiazin-3-one 1-oxide Preparation in analogy to Example 1a from (+)-2-(2-[5-bromo -3-oxapentyloxy]phenyl)-2-isopropyl-4-methyl-2,3-dihydrobenzothiazin-3-one 1-oxide.

$^1$H NMR: $\delta = 6.4-7.6$ (m, 8H), 6.35 (s, 2H), 3.79 (s, 6H), 3.73 (s, 3H), 3.35 (s, 3H), 2.85–4.1 (s, 7H), 1.15 (dd, 6H).

Dihydrochloride: melting point 111°–113° C.

EXAMPLE 25

2-[3-[4-[4-(3,4,5-Trimethoxyphenylacetyl)piperazin-1-yl]butoxy]phenyl]-2-hexyl-4-methyl-2,3-dihydrobenzothiazin-3-one 1-oxide The preparation is carried out in analogy to Example 1a from 2-(3-[4-bromobutoxy]phenyl)-2-hexyl-4-methyl-2,3-dihydrobenzothiazin-3-one 1-oxide and 4-(3,4,5-trimethoxyphenylacetyl)piperazine.

$^1$H NMR: $\delta = 6.5-7.6$ (m, 8H), 6.40 (s, 2H), 3.81 (s, 6H), 3.77 (s, 3H), 3.68 (s, 2H), 3.40 (s, 3H), 1.0–2.0 (m, 12H), 0.85 (t, 3H)

EXAMPLE 26

2-[2-[4-(4-[2-(3,4,5-Trimethoxyphenyl)ethyl]piperazin-1yl]but-2-ynoxy]-5-fluorophenyl]-7-chloro-2-isopropyl-4-methyl-2,3-dihydrobenzothiazin-3-one 1-oxide The preparation is carried out in analogy to Example 1a from 2-(2-[4-chlorobut-2-ynoxy]-5-fluorophenyl)-7-chloro-2-isopropyl-4-methyl-2,3-dihydrobenzothiazin-3-one 1-oxide.

$^1$H NMR: $\delta = 6.4-7.8$ (m, 6H), 6.35 (s, 2H), 4.60 (m, 2H), 3.80 (s, 6H), 3.76 (s, 3H), 3.45 (s, 3H), 1.30 (d, 3H), 1.2 (d, 2H).

We claim:

1. A benzothiazinone oxide of the formula I

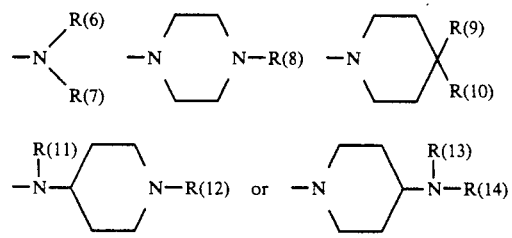

and its salts with pharmaceutically acceptable acids, in which the following substituents and indices have the following meaning:

R(1), R(1)' and R(1)" are identical or different and denote, independently of one another, hydrogen, $(C_1-C_4)$-alkyl, $(C_1-C_3)$-alkoxy, F, Cl, Br, $CF_3$, nitro, hydroxyl, acetamido or amino, R(2) denotes hydrogen, $(C_1-C_{10})$-alkyl, straight-chain or branches, $(C_3-C_{10})$-alkenyl, straight-chain or branches, phenyl-$(C_1-C_4)$-alkly, the phenyl ring being unsubstituted or substituted by one, two or three substituents selected from the group consisting of $(C_1-C_4)$-alkyl, $(C_1-C_3)$-alkoxy, F, Cl, $CF_3$, $(C_1-C_2)$-alkylenedioxy and nitro, R(3) denotes $(C_1-C_{15})$-alkyl, straight-chain or branched, $(C_3-C_{15})$-alkenyl, straight-chain or branched, $(C_4-C_8)$-cycloalkyl, $(C_4-C_8)$-cycloalkyl-$(C_1-C_4)$-alkyl, phenyl or phenyl-$(C_1-C_4)$-alkyl, the phenyl radical being unsubstituted or substituted by one, two or three substituents selected from the group consisting of $(C_1-C_4)$-alkyl, $(C_1-C_3)$-alkoxy, F, Cl, $CF_3$, $(C_1-C_2)$-alkylenedioxy and nitor, R(4)' are identical or different and denote, independently of one another, hydrogen, $(C_1-C_4)$-alkyl, $(C_1-C_3)$-alkoxy, F, Cl, $CF_3$, nitro, hydroxyl, acetamido or amino, A denotes a CH(OH) group, a C=O group, a CH=CH group, a C≡C group, a $CH_2$ group, oxygen or sulfur, m denotes 1 or 2, n denotes 1, 2 or 3, p denotes zero, 1, 2, 3 or 4; but only 2, 3 or 4 where A is a heteroatom; and only 1, 2, 3 or 4 where A is a CH(OH), CH=CH or C≡C group, R(5) denotes one of the following groups

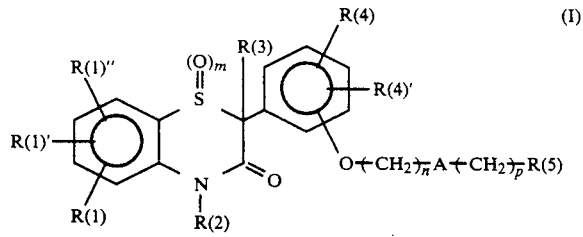

in which

R(6) and R(7) are identical or different or denote, independently of one another, hydrogen, $(C_1-C_{10})$-alkyl, $(C_4-C_8)$-cycloalkyl, $(C_4-C_8)$-cycloalkyl-$(C_1-C_4)$-alkyl, pyridyl-$(C_1-C_4)$-alkyl, phenyl-$(C_1-C_6)$-alkyl, benzhydryl or benzhydrl-$(C_1-C_4)$-alkyl, each of the phenyl radicals being unsubstituted or substituted by one, two or three radicals selected from the group consisting of $(C_1-C_4)$-alkyl, $(C_1-C_4)$-alkoxy, $(C_1-C_2)$-alkylenedioxy, F, Cl, Br, $CF_3$ and hydroxyl, R(8) denotes hydrogen, $(C_1-C_{10})$-alkyl, straight-chain or branched, $(c_1-C_8)$-alkanoyl, pyridyl, pyrimidinyl, phenyl, phenyl-$(C_1-C_4)$-alkyl, phenyl-$(C_3-C_5)$-alkenyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals selected from the group consisting of $(C_1-C_4)$-alkyl, $(C_1-C_4)$-alkoxy, $(C_1-C_2)$-alkylenedioxy, F, Cl, Br, $CF_3$ and hydroxyl, R(9) denotes hydrogen, $(C_1-C_{10})$-alkyl, phenyl, phenyl-$(C_1-C_4)$-alkyl, each of the phenyl radicals being unsubstituted or substituted by one, two or three radicals selectred from the group consisting of $(C_1-C_4)$-alkyl, $(C_1-C_4)$-alkoxy, $(C_1-C_2Z)$-alkylenidioxy, F, Cl, Br, $CF_3$ and hydroxyl, R(10) denotes hydrogen, hydroxyl or $(C_1-C_4)$-alkoxy, and R(11) and R(12) or R(13) and R(14) are identical or different and denote, independently of one another, hydrogen, $(C_1-C_{10}))$-alkyl, straight-chain or branched, $(C_1-C_6)$-alkanoyl, phenyl-$(C_1-C_4)$-alkyl, benzhydrul, or benzhydryl-$(C_1-C_4)$-alkyl, phenyl-$(C_1-C_4)$-alkanoyl or benzoyl, each of the phenyl radicals being unsubstituted or substithe group consisting of ($C_1$-$C_4$)-alkyl, ($C_1$-$C_4$)-alkoxy, ($C_1$-$C_2$)-alkylenedioxy, F, Cl, Br, $CF_3$ and hydroxyl.

2. A compound I as claimed in claim 1, wherein at least one of the substituents of indices has the following meaning:

R(1) and R(1)', identical or different and independently of one another, hydrogen, methyl, ethyl, methoxy, ethoxy, fluorine, chlorine, $CF_3$, nitro or acetamido, R(1)" hydrogen, R(2) hydrogen, ($C_1$—6)-alkyl, straight-chain or branched, allyl, methallyl, benzyl, phenethyl, 4-methoxybenzyl, 3,4-dimethoxybenzyl, 3,4,5-trimethoxybenzyl, 3,4-methylenedioxybenzyl, R(3) ($C_1$-$C_{12}$)-alkyl, straight-chain or branched, allyl, methallyl, ($C_5$-$C_7$)-cycloalkyl, ($C_5$-$C_7$)-cycloalkyl-($C_1$-$C_4$)-alkyl, benzyl, methylbenzyl, fluorobenzyl, methoxybenzyl, dimethoxybenzyl or phenylethyl, R(4) hydrogen, methyl, methoxy, ethoxy, fluorine, chlorine, nitro, hydroxyl, acetamido or amino, R(4)' hydrogen, A a CH(OH) group, a C=O group, a CH=CH group, a C≡C group, a $CH_2$ group, oxygen or sulfur, m 1 or 2, n 1 or 2, p zero, 1, 2 or 3; but only 2 or 3 when A is a heteroatom; and only 1, 2 or 3 where A is a CH(OH), CH=CH or C≡C group, R(5) one of the following groups

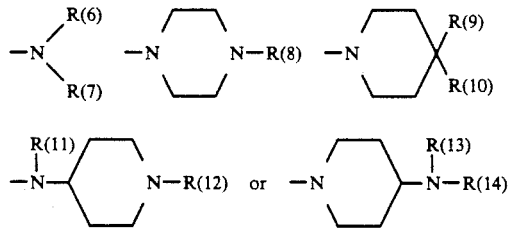

in which

R(6) denotes hydrogen, methyl, ethyl, propyl or isopropyl,

R(7) denotes hydrogen, methyl, ethyl, propyl, isopropyl, cyclopentylethyl, cyclohexylethyl, phenyl-($C_1$-$C_4$)-alkyl, benzhydryl or benzhydryl-($C_1$-$C_4$)-alkyl, each of the phenyl radicals being unsubstituted or substituted by one, two or three radicals selected from the group consisting of ($C_1$-$C_4$)-alkyl, ($C_1$-$C_4$)-alkoxy, ($C_1$—2)-alkylenedioxy, F, Cl, $CF_3$ or hydroxyl, and denotes pyridyl-($C_1$-$C_4$)-alkyl, R(8) denotes hydrogen, ($C_1$-$C_6$)-alkyl, straight-chain or branched, ($C_1$-$C_6$)-alkanoyl, phenyl, the phenyl radical being unsubstituted or substituted by one or two radicals selected from the group consisting of ($C_1$-$C_4$)-alkyl, ($C_1$-$C_4$)-alkoxy, ($C_1$-$C_2$)-alkylenedioxy, F, Cl, $CF_3$ and hydroxyl, or denotes phenyl-($C_1$-$C_4$)-alkyl, phenyl-($C_3$-$C_5$)-alkenyl, benzhydryl or benzhydryl-($C_1$-$C_4$)-alkyl, phenyl-($C_1$-$C_4$)-alkanoyl or benzoyl, each of the phenyl radicals being unsubstituted or substituted by one, two or three radicals selected from the group consisting of methyl, ethyl, methoxy, ethoxy, ($C_1$-$C_2$)-alkylenedioxy, F, Cl, $CF_3$ and hydroxyl, R(9) denotes phenyl, phenyl-($C_1$-$C_4$)-alkyl, each of the phenyl radicals being unsubstituted or substituted by one, two or three radicals selected from the group consisting of ($C_1$-$C_4$)-alkyl, ($C_1$-$C_4$)-alkoxy, ($C_1$-$C_2$)-alkylenedioxy, F, Cl, $CF_3$ or hydroxyl, R(10) denotes hydrogen, hydroxyl or methoxy, R(11), R(12), R(13) and R(14) are identical or different and denote hydrogen, ($C_1$-$C_8$)-alkyl, ($C_1$-$C_6$)-alkanyl, phenyl-($C_1$-$C_4$)-alkyl, benzhydryl or benzhydryl-($C_1$-$C_4$)-alkyl, phenyl-($C_1$-$C_4$-)-alkanoyl or benzoyl, each of the phenyl radicals being unsubstituted or substituted by one, two or three radicals selected from the group consisting of methyl, ethyl, methoxy, ethoxy, ($C_1$-$C_2$)-alkylenedioxy, F, Cl, $CF_3$ and hydroxyl, 3. A compound I as claimed in claim 1, wherein at least one of the substituents or indices has the following meaning:

R(1) hydrogen, methyl, methoxy, fluorine or chlorine,

R(1)' hydrogen or methoxy,

R(1)" hydrogen,

R(2) hydrogen, methyl, ethyl, propyl, isopropyl, butyl, sec.butyl, isobutyl, benzyl or phenethyl, R(3), ($C_1$-$C_{12}$)-alkyl, straight-chain or branched, cyclopentyl, cyclohexyl, cyclopentylmethyl, cyclohexylmethyl, allyl, methallyl, benzyl, methylbenzyl, fluorobenzyl, methoxybenzyl, dimethoxybenzyl or phenylethyl, R(4) hydrogen, methoxy, methyl, fluorine, chlorine, nitro or hydroxyl, R(4)' hydrogen, A a CH(OH) group, a C=O group, a CH=CH group, a C≡C group, a $CH_2$ group or oxygen, m 1 or 2, n 1 or 2, p zero, 1 or 2; but only 2 when A is a heteroatom; and only 1 or 2 where A is a CH(OH), CH=CH or C≡C group, R(5) one of the following groups

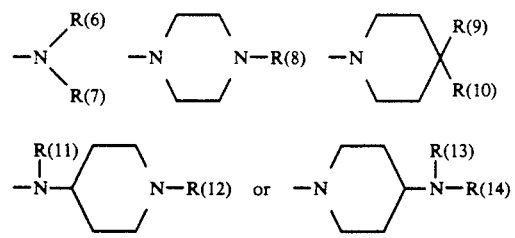

in which

R(6) denotes hydrogen or methyl,

R(7) denotes phenyl-($C_1$-$C_4$)-alkyl, benzhydryl or benzhydrul-($C_1$-$C$-4)-alkyl, each phenyl radical being unsubstituted or substituted by one, two or three radicals selected from the group consisting of methyl, methoxy, fluorine, chlorine, methylenedioxy or hydroxyl, R(8) denotes ($C_1$-$C_6$)-alkyl, straight-chain or branched, ($C_1$-$C_6$)-alkanoyl, phenyl, phenyl-($C_1$-$C_4$)-alkyl, benzhydryl or benzhydryl-($C_1$-$C_4$)-alkyl, phenyl($C_1$-4)-alkanoyl or benzoyl, each of the phenyl radicals being unsubstituted or substituted by one, two or three radicals selected from the group consisting of methyl, methoxy, ethoxy, methylenedioxy, fluorine, chlorine or hydroxyl, R(9) denotes phenyl, the phenyl radical being unsubstituted or substituted by one, two or three radicals selected from the group consisting of methyl, methoxy, fluorine, chlorine, methylenedioxy and hydroxyl, R(10) denotes hydrogen, hydroxyl or methoxy, R(11), R(12), R(13) and R(14) are identical or different and denote $(C_1-C_6)$-alkyl, $(C_1-C_6)$-alkanoyl, phenyl-$(C_1-C_4$-$)$-alkyl, benzhydryl benzhydryl-$(C_1-C_4)$-alkyl, phenyl-$(C_1-C_4)$-alkanoyl or benzoyl, each of the phenyl radicals being unsubstituted or substituted by one, two or three radicals selected from the group consisting of methyl, methoxy, methylenedioxy, fluorine, chlorine or hydroxyl.

4. A pharmaceutical composition for the treatment of diseases of the cardiovascular system which containsk a compound of the formula I as claimed in cliam 1 together with a pharmaceutically acceptable vehicle.

5. A method for the treatment of diseases of the cardiovascular system which comprises administering an effective amount for said treatment of a compound of the formula I as claimed in claim 1.

* * * * *